US009010819B2

(12) United States Patent
Mueller et al.

(10) Patent No.: US 9,010,819 B2
(45) Date of Patent: Apr. 21, 2015

(54) REMOVABLE SPECIMEN GRIPPER FINGERS

(71) Applicant: Beckman Coulter, Inc., Brea, CA (US)

(72) Inventors: Martin Mueller, Schliersee-Neuhaus (DE); Sophia Lauterbach, Buxheim (DE)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/055,479

(22) Filed: Oct. 16, 2013

(65) Prior Publication Data

US 2014/0103674 A1  Apr. 17, 2014

Related U.S. Application Data

(60) Provisional application No. 61/790,446, filed on Mar. 15, 2013, provisional application No. 61/714,656, filed on Oct. 16, 2012.

(51) Int. Cl.
| *B25J 15/04* | (2006.01) |
| *B25J 15/10* | (2006.01) |
| *B65G 11/02* | (2006.01) |
| *A61B 19/02* | (2006.01) |

(Continued)

(52) U.S. Cl.
CPC ............ B25J 15/103 (2013.01); B65G 11/023 (2013.01); A61B 19/0287 (2013.01); G01F 23/0061 (2013.01); B25J 15/0475 (2013.01); G01F 23/2962 (2013.01); G01N 35/00732 (2013.01); G01N 35/0099 (2013.01); Y10T 29/49826 (2013.01); G01S 15/04 (2013.01)

(58) Field of Classification Search
CPC .... B25J 15/04; B25J 15/0408; B25J 15/0475; B25J 15/103; Y10S 483/901
USPC .......................... 294/86.4, 213, 902; 901/39; 269/280–284; 483/1, 69
See application file for complete search history.

(56) References Cited

U.S. PATENT DOCUMENTS 3,135,396 A * 6/1964 Grainger ........................... 414/8
4,579,380 A   4/1986 Zaremsky et al.
(Continued)

FOREIGN PATENT DOCUMENTS

DE  34 20 857 A1  12/1985
GB  2 147 268 A   5/1985
(Continued)

OTHER PUBLICATIONS

Anonymous; "Workpiece Gripper,"; *IBM Technical Disclosure Bulletin*; Jun. 1, 1985; vol. 28; No. 1; pp. 327-328.
(Continued)

*Primary Examiner* — Dean Kramer
(74) *Attorney, Agent, or Firm* — Kilpatrick Townsend & Stockton LLP

(57) ABSTRACT

Systems and methods for gripper finger release assemblies for specimen gripper units are disclosed. Embodiments of the invention include release elements to enable replacement of gripper fingers without the need of tools or without the need to demount and mount the entire gripper unit for exchange of gripper fingers. A release element may comprise a first sliding element and a second sliding element coupled to a plate such that pressing the second sliding element enables the first sliding element to release a gripper finger coupled to the first sliding element.

12 Claims, 11 Drawing Sheets

(51) Int. Cl.
  *G01F 23/00* (2006.01)
  *G01F 23/296* (2006.01)
  *G01N 35/00* (2006.01)
  *G01S 15/04* (2006.01)

(56) References Cited

U.S. PATENT DOCUMENTS

| | | | |
|---|---|---|---|
| 4,645,407 A | | 2/1987 | Williams |
| 4,676,541 A | | 6/1987 | Lord et al. |
| 4,715,636 A | * | 12/1987 | Wiesner et al. ............. 294/86.4 |
| 5,171,979 A | | 12/1992 | Kwa et al. |
| 5,256,128 A | * | 10/1993 | Neumann ....................... 483/1 |
| 5,360,249 A | * | 11/1994 | Monforte et al. .......... 294/119.1 |
| 5,455,006 A | | 10/1995 | Aota et al. |
| 5,918,739 A | | 7/1999 | Bilof et al. |
| 5,941,366 A | | 8/1999 | Quinlan et al. |
| 6,257,091 B1 | | 7/2001 | Cohen et al. |
| 6,293,750 B1 | | 9/2001 | Cohen et al. |
| 6,539,334 B1 | | 3/2003 | Sawafta |
| 6,859,271 B1 | | 2/2005 | Carney et al. |
| 7,473,897 B2 | | 1/2009 | Braendle et al. |
| 7,688,448 B2 | | 3/2010 | Bamberg et al. |
| 8,267,451 B2 | | 9/2012 | Pedrazzini |
| 8,382,177 B2 | | 2/2013 | Rizk et al. |
| 2007/0080223 A1 | | 4/2007 | Japuntich |
| 2007/0258858 A1 | | 11/2007 | Rasnow et al. |
| 2007/0289660 A1 | | 12/2007 | Aylward |
| 2008/0047369 A1 | | 2/2008 | Tsujimura et al. |
| 2008/0122155 A1 | | 5/2008 | Wieland |
| 2008/0286082 A1 | | 11/2008 | Moran et al. |
| 2009/0047179 A1 | | 2/2009 | Ping et al. |
| 2009/0315281 A1 | * | 12/2009 | Tuauden et al. ............. 279/142 |
| 2010/0066109 A1 | | 3/2010 | Pedrazzini |
| 2010/0101317 A1 | | 4/2010 | Ashrafzadeh et al. |
| 2010/0111384 A1 | | 5/2010 | Nagai et al. |
| 2010/0261595 A1 | | 10/2010 | Schaefer et al. |
| 2010/0314895 A1 | * | 12/2010 | Rizk et al. ..................... 294/106 |
| 2011/0065193 A1 | | 3/2011 | Kitagawa et al. |
| 2011/0089709 A1 | | 4/2011 | Neeper |
| 2011/0262896 A1 | | 10/2011 | Blecka et al. |
| 2012/0013889 A1 | | 1/2012 | Heise |
| 2012/0058900 A1 | | 3/2012 | Gisler et al. |
| 2013/0020820 A1 | | 1/2013 | Bieler |
| 2013/0149079 A1 | | 6/2013 | Ohiso et al. |

FOREIGN PATENT DOCUMENTS

| | | | |
|---|---|---|---|
| GB | 2 191 466 | * | 12/1987 |
| WO | 00/38046 A1 | | 6/2000 |
| WO | 2006/075201 A1 | | 7/2006 |
| WO | 2012/029834 A1 | | 3/2012 |

OTHER PUBLICATIONS

Dukhyun, Kang et al.; "Shape Recognition by Random Grasping,"; *Proceedings of the 1992 IEEE/RSJ International Conference on Intelligent Robots and Systems*; Jul. 7-10, 1992, Raleigh NC; pp. 387-392.

Notash, Leila et al.; "Kinermatic Calibration of Parallel Manipulators,"; *IEEE International Connference on Intelligent Systems for the 21st Century*; Oct. 22-25, 1995, Vancouver, BC, Canada; pp. 3310-3315.

International Search Report and Written Opinion mailed on Dec. 6, 2013 for PCT Patent Application No. PCT/US2013/053848, 15 pages.

International Search Report and Written Opinion mailed on Feb. 26, 2014 for PCT Patent Application No. PCT/US2013/065216, 11 pages.

International Search Report and Written Opinion mailed on Feb. 26, 2014 for PCT Patent Application No. PCT/US2013/065255, 11 pages.

International Search Report and Written Opinion mailed on Mar. 27, 2014 for PCT Patent Application No. PCT/US2013/065213, 11 pages.

International Search Report and Written Opinion mailed on Mar. 17, 2014 for PCT Patent Application No. PCt/US2013/065280, 14 pages.

* cited by examiner

REMOVABLE SPECIMEN GRIPPER FINGERS

CROSS-REFERENCES TO RELATED APPLICATIONS

This application claims priority to U.S. Provisional Application No. 61/790,446 filed Mar. 15, 2013 and entitled "Specimen Gripper." This application further claims priority to U.S. Provisional Application No. 61/714,656 filed Oct. 16, 2012 and entitled "Specimen Gripper." All of these applications are herein incorporated by reference in their entirety for all purposes.

BACKGROUND

Conventional medical laboratory systems contain many segments for processing patient samples, some of which are automated and some of which require manual operation. Laboratory systems today have become more efficient due to those segments which have become automated. However, there are still several components of medical laboratory systems that can be automated in order to reduce the need for manual operation of the system and reduce the space required by machinery.

Use of robot arms in various areas of a laboratory system is known. A robotic arm unit can couple to a specimen gripper or a gripper unit for gripping specimen containers using gripper fingers. However, the gripper fingers of the gripper unit may not be easily replaceable. For example, the gripper fingers may need to be repaired due to wear or service. In some cases, the specimen gripper may need to perform different functions using special gripper fingers customized for each function. This may require frequently exchanging the gripper fingers. For example, a specimen gripper may be used as a tube gripper, a recapper or a decapper in a laboratory automation system. It may be desirable to change the gripper fingers in a specimen gripper in these situations.

In some cases, the entire gripper unit may need to be demounted and remounted when the gripper fingers need to be replaced or repaired. Additionally, mounting or demounting of the fingers may require tools (e.g., a screw driver) and a certain amount of time (e.g., for removal of the screws). This can lead to sample processing delays. In such cases, it is desirable to have the flexibility of quickly and easily replacing the gripper fingers without requiring tools, such as a screw driver, or without the need to demount the entire gripper for exchange of the fingers.

Embodiments of the invention provide systems and methods for the quick exchange of gripper fingers without the need of tools.

BRIEF SUMMARY

Embodiments of the technology relate to systems and methods for gripper finger release assemblies for specimen grippers.

An embodiment is directed to a gripper unit comprising a release element, a first gripper finger comprising a first cavity and a mounting structure comprising a second cavity, wherein the first gripper finger is removably coupled to the mounting structure by the release element. The release element further comprises a plate and a first sliding element coupled to the plate. The first sliding element may be configured to pass through the first and second cavities to secure the first gripper finger to the mounting structure.

One embodiment is directed to a system comprising a gripper unit. The gripper unit further comprises a release element, a first gripper finger comprising a first cavity and a mounting structure comprising a second cavity, wherein the first gripper finger is removably coupled to the mounting structure by the release element. The release element further comprises a plate and a first sliding element coupled to the plate. The first sliding element may be configured to pass through the first and second cavities to secure the first gripper finger to the mounting structure.

Another embodiment is directed to a gripper unit comprising a release element, a first gripper finger and a mounting structure, wherein the first gripper finger is removably coupled to the mounting structure by the release element. The release element further comprises a connection plate, a first sliding element coupled to the connection plate, wherein the first sliding element is configured to removably couple to the first gripper finger. The release element also comprises a second sliding element coupled to the connection plate, wherein the second sliding element is configured to enable the first sliding element to release the first gripper finger when the second sliding element is pressed.

Another embodiment is directed to a method comprising removably coupling a first gripper finger comprising a first cavity to a mounting structure comprising a second cavity by a release element, wherein the release element comprises a plate, a first sliding element coupled to the plate and a second sliding element coupled to the plate, and wherein the first sliding element is configured to pass through the first and second cavities to secure the first gripper finger to the mounting structure. The method further comprises pressing the second sliding element to release the first gripper finger, aligning a third cavity on a second gripper finger with the first sliding element after the first gripper finger has been released, and removably coupling the second gripper finger to the first sliding element by releasing the second sliding element.

These and other embodiments of the technology are described in further detail below.

BRIEF DESCRIPTION OF THE DRAWINGS

A further understanding of the nature and advantages of the different embodiments may be realized by reference to the following drawings.

DETAILED DESCRIPTION

Figure 1:
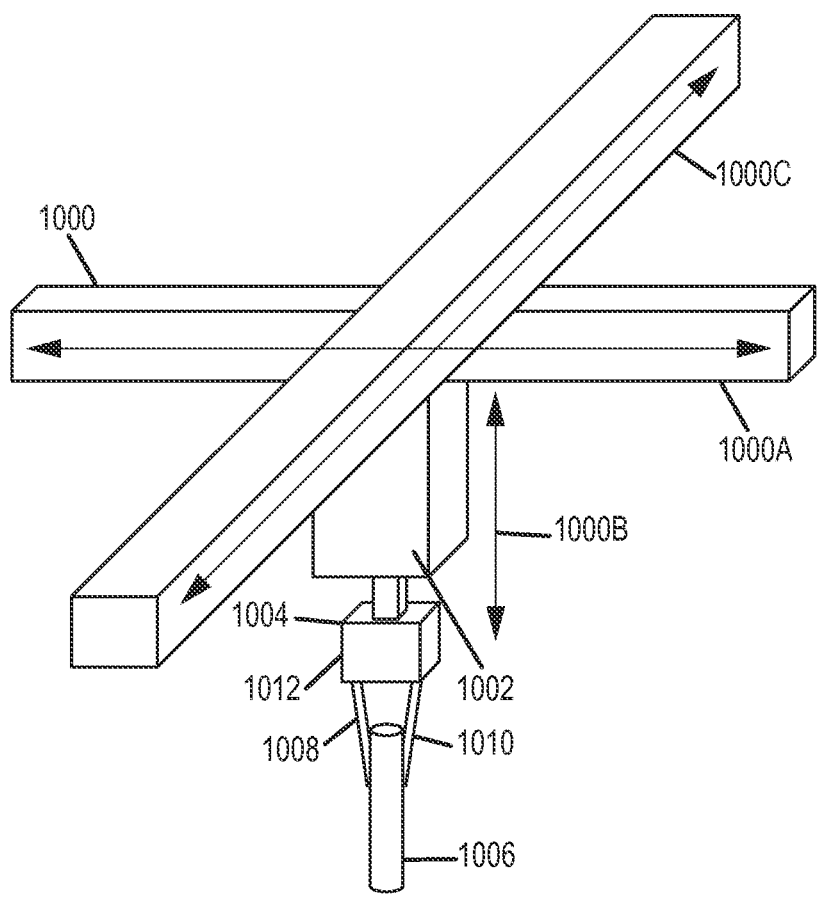
FIG. 1 depicts an example of a Cartesian or gantry robot with three independently moveable directions x-,y-, and z-.

Specimen gripper units are generally used in laboratory automation systems to perform different functions. For example, a specimen gripper unit may be used to grip specimen containers such as sample tubes. A specimen gripper unit may also be used as a decapper for removing caps from the specimen containers or as a recapper for attaching caps to the specimen containers. In such cases, the specimen gripper unit may require specialized gripper fingers to perform different functions. However, the gripper fingers of a specimen gripper unit may not be easily replaceable. Further, in some case, exchanging the gripper fingers may involve loose parts, such as screws or pins. Additionally, mounting or demounting of the fingers may require tools (e.g., a screw driver) and a certain amount of time (e.g., for removal of the screws). In order to demount the fingers, it may be necessary to destroy the parts, such as pins, that couple the gripper fingers to a body of the specimen gripper. Further, in some cases, screws can fall into the system during removal of the fingers. Such problems can lead to sample processing delays since the specimen gripper unit may not be usable during that period.

Embodiments of the invention include devices to enable replacement of gripper fingers without the need of tools or without the need to demount the entire gripper unit for exchange of gripper fingers.

A specimen gripper may have or couple to a plurality of gripper fingers including a first gripper finger, a second gripper finger, etc. In some embodiments, the plurality of gripper fingers comprises three gripper fingers. Each gripper finger may take a form of an elongated structure that is capable of gripping an object such as a sample tube in collaboration with one or more other gripper fingers. In some embodiments, an exemplary gripper finger may have a rectangular, axial and/or longitudinal, cross-section with predetermined thickness (e.g., one quarter of an inch or more) and length (e.g., three inches or more). Suitable gripper fingers may be rigid or may have one or more pivoting regions. In some embodiments, a jaw may be coupled to one end (gripping end) of the gripper finger to aid in gripping the object. The other end of the gripper finger may be coupled to an assembly in a body along with other gripper fingers that may be operable to control the gripper fingers for gripping the object, such as, a sample tube or a cap.

In some embodiments of the invention, a gripper finger may comprise means for coupling to a gripper finger release assembly that can enable a quick exchange of the gripper finger. For example, a gripper finger may comprise a cavity or a hole for coupling to a release assembly and to the specimen gripper. Note that in this specification, the term "gripper finger" may imply that the gripper finger is replaceable or removable and may be used interchangeably with "removable gripper finger" or "replaceable gripper finger."

A "cavity" may include a hole or an opening through which an object can pass through. In one embodiment, a cavity may be a hole in a gripper finger through which a sliding element can pass through for coupling the gripper finger to a specimen gripper. The dimensions of the cavity may be such so as to allow the sliding element to easily slide through the cavity. In one embodiment, a cavity may have a circular cross-section with a diameter slightly bigger than the diameter of the sliding element (e.g., if the sliding element is cylindrical in shape with a circular cross-section). In one embodiment, the length of the cavity may depend upon the width of the gripper finger where the cavity is located. In embodiments of the invention, a cavity may be located at or near the non-gripping end of the gripper finger, where the gripper finger is coupled to the specimen gripper.

In some embodiments, a cavity may also be a hole in a mounting structure of the specimen gripper. In one embodiment, there may be plurality of cavities in the mounting structure for allowing the coupling of the plurality of gripper fingers to the body of the specimen gripper. In some embodiments, a gripper finger release assembly may couple to the mounting structure of the specimen gripper via two cavities, where each cavity may have different dimensions.

Specimen grippers may be used in a medical laboratory system for processing patient samples. In some embodiments, a specimen gripper may be coupled to a robotic arm. Robotic arms may be used for transportation of specimen containers in various areas of a laboratory system, such as input, distribution, centrifuge, decapper, aliquotter, output, sorting, recapping, and secondary tube lift areas.

A specimen container that is manipulated by the gripper unit may be a sample tube with or without a cap. An exemplary sample tube may contain material for medical analysis, such as blood, serum, gel, plasma, etc. In some embodiments, the sample tube may need to be decapped or recapped for storage, processing, discarding, etc.

The robotic arm architecture can differ in complexity dependent upon the given task. FIG. 1 depicts an example of a Cartesian or gantry robot with three independently moveable directions x-, y-, and z-. The gantry robot 1000 shown in FIG. 1 shows a simple robotic arm 1002 that can move up and down. More complex robotic arms may include, for example, a Selective Compliant Assembly Robot Arm (SCARA) or an articulated robotic arm with multiple joint arms.

In some embodiments of the invention, a specimen gripper unit 1004, may be coupled to the robot arm 1002. The robot arm 1002 may be part of the gantry robot 1000 that is configured to move independently in three, orthogonal directions denoted as 1000A, 1000B and 1000C. As the specimen gripper unit 1004 is transported by the robot arm 1002, the specimen gripper unit 1004 may transport a specimen container 1006 held by fingers 1008 of the specimen gripper unit 1004.

The specimen gripper unit 1004 may have two or more moveable gripper fingers 1008, 1010 coupled to a body 1012 to grip the specimen container 1006. For example, the gripper fingers 1008, 1010 may move inwardly toward the specimen container 1006 until the specimen container 1006 is held in a fixed position between the gripper fingers 1008 and 1010. The gripper fingers 1008, 1010 may also be configured to spread outwardly to release the specimen container 1006. Embodiments of the invention provide an assembly to replace the gripper fingers 1008, 1010 without demounting or mounting the specimen gripper unit 1004 and without the need of tools. The robot arm 1002 may be part of a laboratory automation system as further described with reference to FIG. 2.

Figure 2:
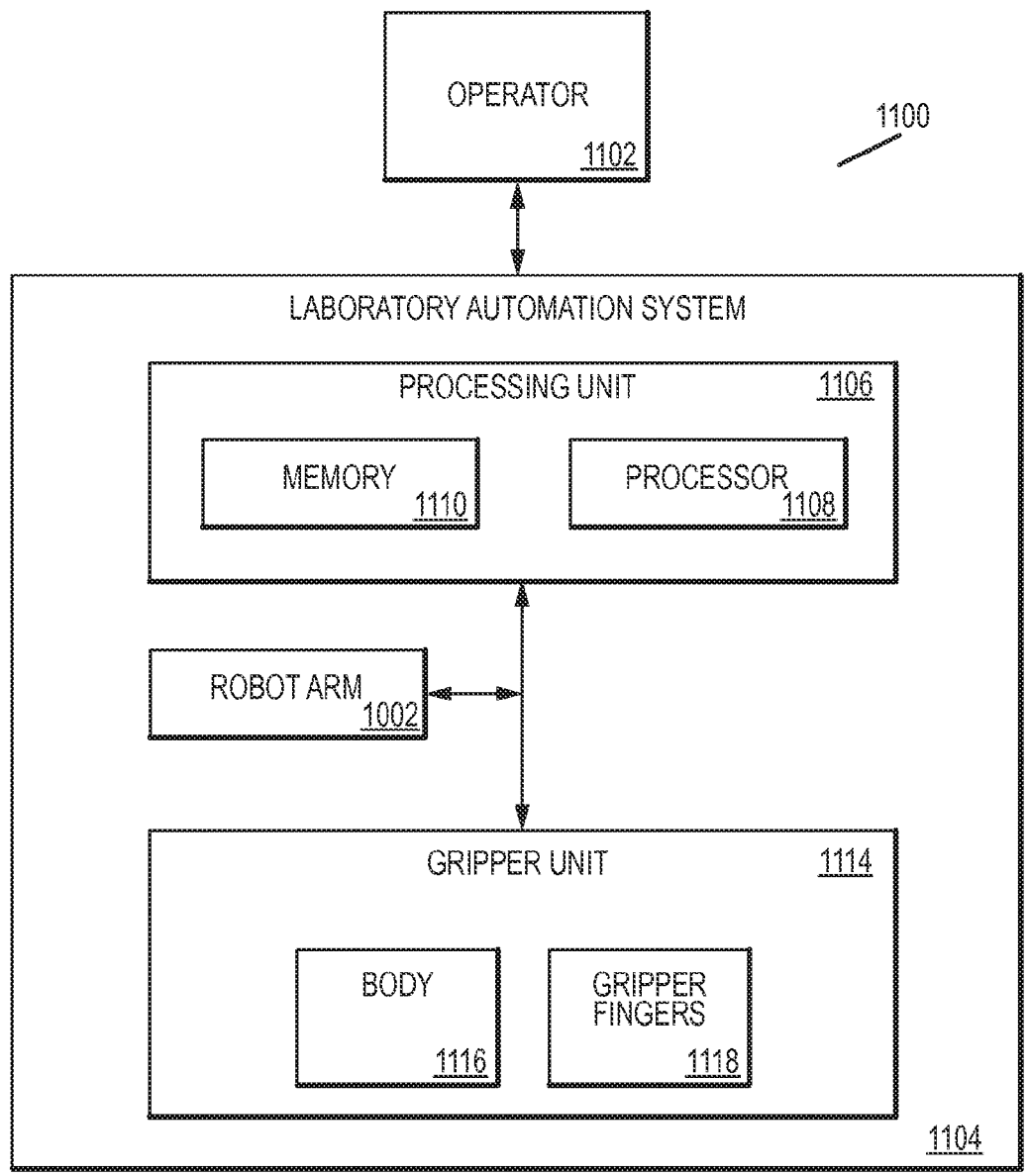
FIG. 2 illustrates a block diagram of a system that may be utilized in a medical laboratory.

FIG. 2 illustrates a block diagram of a system 1100 that may be utilized in a medical laboratory. The system 1100 may include an operator 1102 that may be operable to communicate with a laboratory automation system 1104 for processing of samples (e.g., serum, plasma, gel, packed red blood cells, etc.). In the exemplary embodiment, the laboratory automation system 1104 includes the robot arm 1002, a processing unit 1106 and a gripper unit 1114. However, a number of other units (not shown) may be utilized by the laboratory automation system 1104. For example, the laboratory automation system 1104 may include an input module, a distribution area, a centrifuge, a decapper, a serum indices measurement device, an aliquotter and/or an output/sorter. The robot arm 1002 may be part of the gantry robot 1000 shown in FIG. 1. The laboratory automation system 1104 may utilize the robot arm 1002 and the gripper unit 1114 to grip a specimen container (e.g., sample tube). Note that the gripper unit 1114 is similar to the specimen gripper 1004 of FIG. 1, and the terms "gripper unit" and the "specimen gripper" may be used interchangeably in this specification.

The gripper unit 1114 may include a body 1116, and gripper fingers 1118 that may be coupled to the body 1116. The body 1116 may include a housing as well as other mechanical and electrical parts that allow the gripper unit 1114 to function. The gripper unit 1114 may also be configured to communicate with the processing unit 1106.

In some embodiments, the gripper unit 1114 may include a sensor unit (not shown) comprising one or more sensors to detect/provide information associated with the specimen gripper that may be used by the processing unit 1106 for efficient processing of samples. For example, a sensor unit comprising one or more sensors may be configured to detect the absence of the gripper fingers 1118 (e.g., during the exchange of the gripper fingers) so that the processor 1108 may disable the robot arm 1002 and/or the gripper unit 1114 for normal operation. It will be understood that the gripper unit 1114 may also include or interface with other units to enable the gripper unit 1114 perform the intended function.

In one embodiment, the body 1116 may include a support structure or a housing, and may be made from any suitable material. It may have any suitable shape including a square or rectangular cross section (e.g., an axial or longitudinal cross-section). The gripper fingers 1118 can be capable of moving with respect to the body 1116. In one embodiment, the body 1116 may include one or more mounting structures so that the gripper fingers 1118 are coupled to the one or more mounting structures. In some embodiments, the body 1116 may include or be coupled to a gripper finger release assembly comprising one or more release elements. This release assembly allows one to easily and quickly exchange gripper fingers without using tools.

The processing unit 1106 may include a processor 1108, and a memory 1110. In some embodiments, the processor 1108 may include other suitable processing elements (not shown), such as one or more of a microprocessor, a digital signal processor, a graphics processor, a co-processor, etc. The processor 1108 may be configured to execute instructions or code in order to implement methods, processes or operations in various embodiments. The processor 1108 may also be configured to enable the robot arm 1002 to move the gripper unit 1114 to function as a tube gripper, a recapper or a decapper. In some embodiments, the processor 1108 can also be configured to disable movement of the gripper unit 1114 by the robot arm 1002 when the gripper fingers need to be exchanged. In some embodiments, the processing unit 1106 may be part of a computer system as described with reference to FIG. 9.

The memory 1110 may be electrically and operatively coupled to the processor 1108 internally or externally (e.g., cloud based data storage) and may comprise any combination of volatile and/or non-volatile memory such as, for example, buffer memory, RAM, DRAM, ROM, flash, or any other suitable memory device. In some embodiments, the memory 1110 may include a computer readable medium (CRM), and may comprise code, executable by the processor 1108 for implementing methods described herein.

The memory 1110 may also store other information. For example, such information may include data related to different types of gripper fingers that may be coupled to the specimen gripper for performing different functionalities. For example, when the specimen gripper is used as a tube gripper, a first set of gripper fingers may be used, whereas, when the specimen gripper is used as a decapper, a second set of gripper fingers may be used, and, when the specimen gripper is used as a recapper, a third set of gripper fingers may be used, etc. In some embodiments, information stored in the memory may also include data related to different types of release elements that may be used for exchange of gripper fingers.

Figure 3:
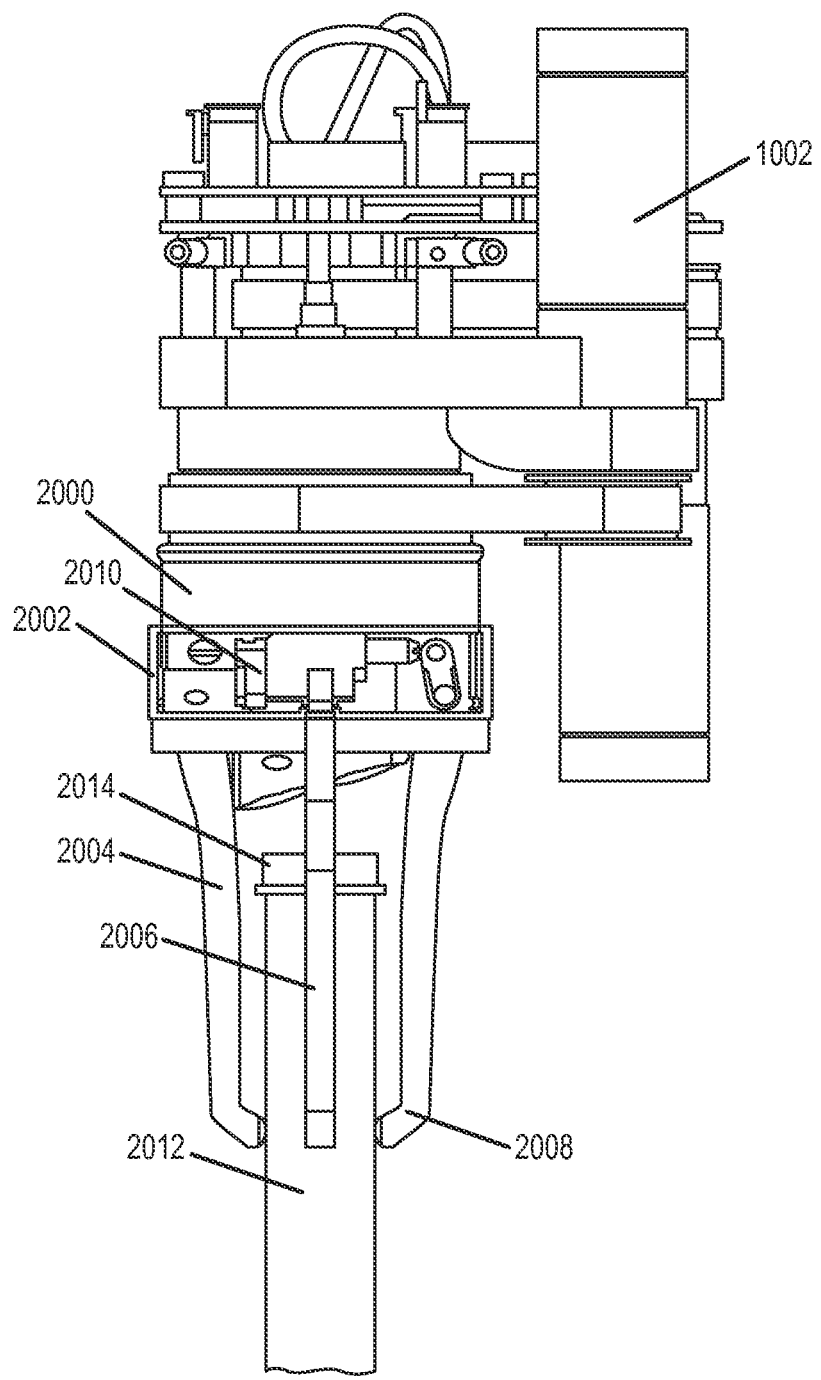
FIG. 3 depicts a gripper unit that provides the capability for quick exchange of gripper fingers, in one embodiment of the invention.

FIG. 3 depicts a gripper unit 2000 that provides the capability for quick exchange of gripper fingers, in one embodiment of the invention.

The gripper unit 2000 may include a body 2002 and removable gripper fingers 2004, 2006, 2008. The gripper unit 2000 may be similar to the gripper unit 1114 and may be coupled to the robot arm 1002 and the processing unit 1106. It will be understood that the gripper unit 2000 may be coupled to other units or modules in the laboratory automation system 1104 for performing the intended functions. The body 2002 may be coupled to a gripper finger release assembly 2010 so that the gripper fingers 2004, 2006, 2008 can be quickly exchanged. It is to be understood that the body 2002 may include or couple to other components or structures suitable for performing the intended function of the gripper unit 2000, for example, as a tube gripper, a recapper or a decapper.

In some embodiments, the gripper finger release assembly 2010 may include one or more release elements. The release elements can couple and uncouple the gripper fingers 2004, 2006, 2008 from the body 2002 without demounting or uncoupling the gripper finger release assembly 2010 from the body 2002 and without using special tools.

In some embodiments, a sample tube 2012 may be gripped by the removable gripper fingers 2004, 2006, 2008. In one embodiment, the sample tube 2012 may have a cylindrical shape with a circular cross-section. In some embodiments, the sample tube 2012 may have a cap 2014. The cap 2014 may have a cylindrical shape with a circular cross-section and a diameter slightly larger than the diameter of the sample tube 2012 and a length relatively shorter than the length of the sample tube 2012. It will be understood that other shapes and sizes of the sample tube 2012 and the cap 2014 are possible that can be gripped by the gripper unit 2000. In some embodiments, a replaceable jaw may be coupled to one end (gripping end) of each of the gripper fingers 2004, 2006, 2008 for accommodating different types of sample tubes or caps.

In some embodiments of the invention, each of the gripper fingers 2004, 2006 and 2008 may comprise a cavity so that each of the gripper finger can couple to a release element in the gripper finger release assembly 2010 to enable a quick exchange of the gripper finger.

Figure 4A:
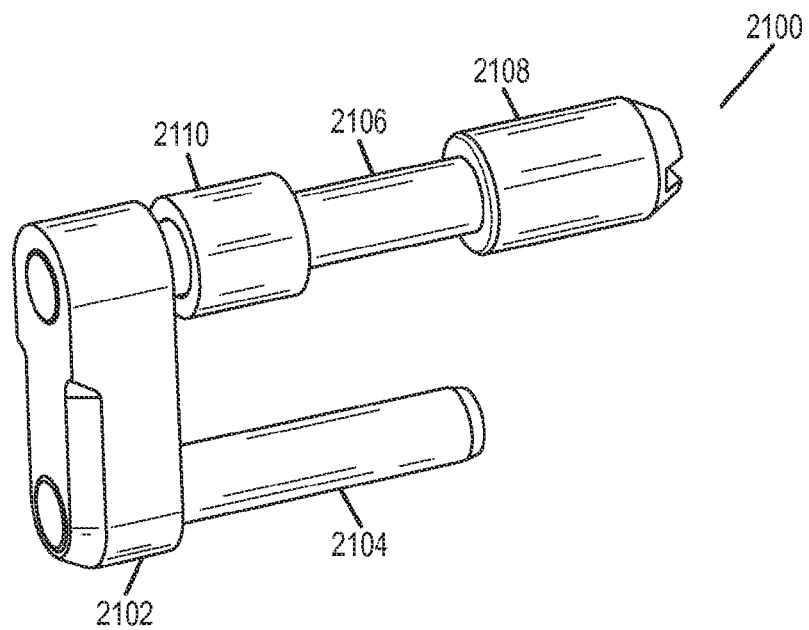
FIGS. 4A-4C illustrate a release element in a first embodiment of the invention.
Figure 4B:
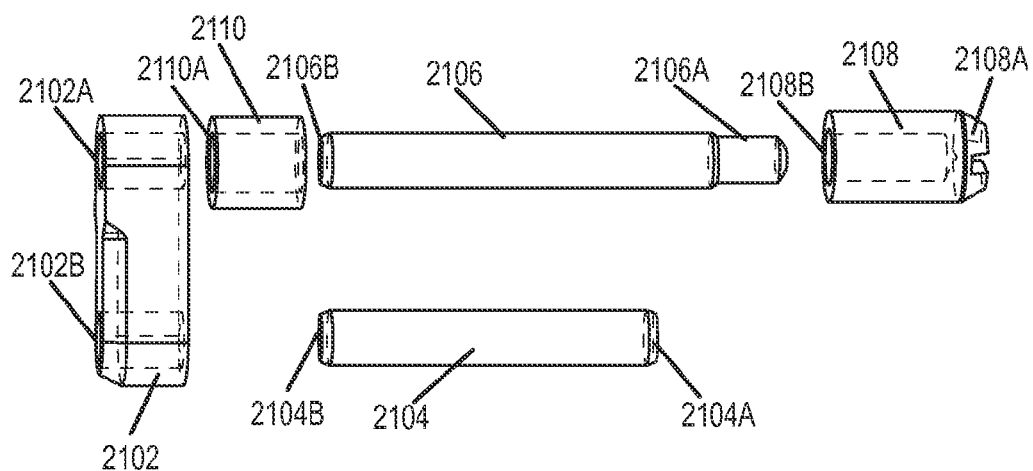
Figure 4C:
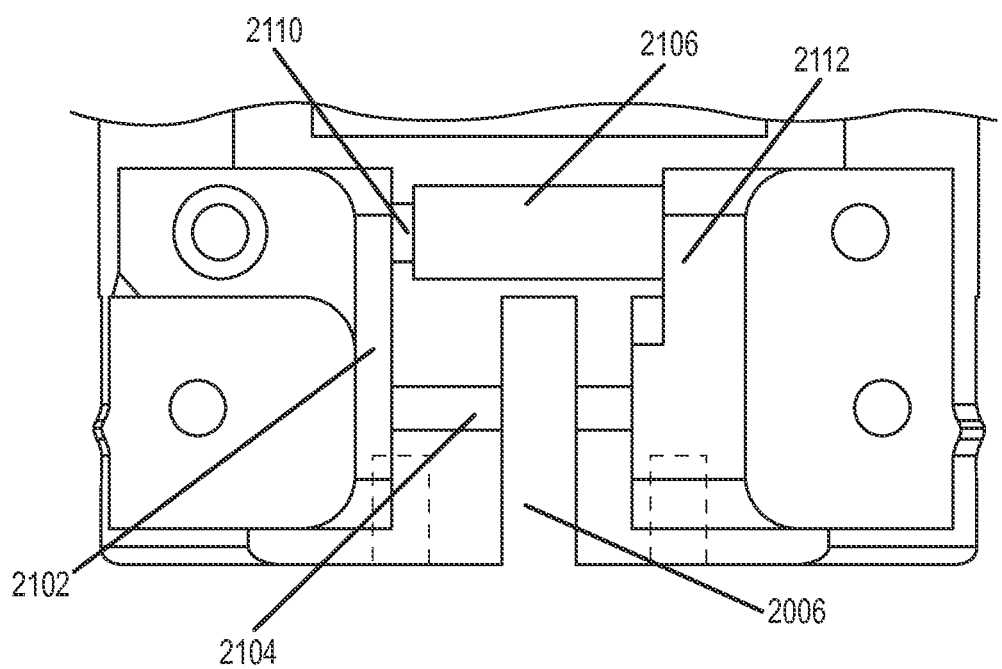

FIGS. 4A-4C illustrate a release element 2100 according to a first embodiment of the invention.

In some embodiments of the invention, the release element 2100 may be part of the gripper finger release assembly 2010 that may be coupled to the body 2002 of the gripper unit 2000.

As illustrated in FIG. 4A, the release element 2100 may include a connection plate (or plate) 2102, a first sliding element 2104, a second sliding element 2106, a cap 2108 and a spring 2110. Different components of the release element 2100 are further described with reference to FIG. 4B. In one embodiment, the release element 2100 may be coupled to a mounting structure 2112, as illustrated in FIG. 4C. A gripper finger may be coupled to the first sliding element 2104 and to the mounting structure 2112. In some embodiments, the first sliding element 2104, the second sliding element 2106, the cap 2108 and the spring 2110 may have a circular, radial cross-sections. In one embodiment, the release element 2100 may be configured to allow the exchange of each of the gripper fingers 2004, 2006, 2008 without demounting or mounting the gripper finger release assembly 2010 and without the need to use tools.

In some embodiments, the connection plate 2102 may be coupled to the first sliding element 2104 and the second sliding element 2106. The connection plate 2102 may be coupled so that the first and second sliding elements 2104, 2106 may be removed from the connection plate 2102, or they may be integral with the connection plate 2102. As shown in FIG. 4A, the connection plate 2102, the first sliding element 2104, and the second sliding element 2106 may form a U-shape. The connection plate 2102 may be configured so that the first sliding element 2104 and the second sliding element 2106 are aligned and connected so that gripper fingers 2004, 2006, 2008 can be exchanged.

As illustrated in FIG. 4B, the connection plate 2102 may have a rectangular cross-section (viewed from its side) and may have two cavities 2102A, 2102 B. In some embodiments, each of the cavities 2102A, 2102 B may have a circular cross-section and they are configured to accommodate and receive a portion of the first sliding element 2104 and a portion of the second sliding element 2106, respectively. The cavities 2102A, 2102 B may each be of any suitable length.

In one embodiment of the invention, the first sliding element 2104 may be cylindrical in shape with a circular, radial cross-section. The first sliding element 2104 may also have any suitable length (e.g., two or more inches in length). The first sliding element 2104 may also be called a "finger pin" in some embodiments.

The first sliding element 2104 may be configured so that a first end 2104A of the first sliding element 2104 can pass through a cavity in a removable gripper finger (not shown in FIGS. 4A and 4B) and a cavity in the mounting structure 2112 to secure the gripper finger to the mounting structure 2112. A diameter of the first sliding element 2104 including the first end 2104A may be slightly smaller than a diameter of the cavity in the removable gripper finger so that the gripper finger can slide on the first sliding element 2104. A second end 2104B of the first sliding element 2104 can couple to the connection plate 2102 through the cavity 2102B. The diameter of the first sliding element 2104 including the second end 2104B can be slightly smaller than the cavity 2102B so that the first sliding element 2104 can pass through the cavity 2102B. In one embodiment of the invention, the first sliding element 2104 is permanently coupled to the connection plate 2102 via the cavity 2102B.

In one embodiment of the invention, the second sliding element 2106 may also be cylindrical in shape and may have a circular radial cross-section and may be slightly longer than the first sliding element 2104. The second sliding element 2106 may also be called a "push screw" in some embodiments. The second sliding element 2106 may be configured so that a first end 2106A of the second sliding element 2106 is slightly smaller than the rest of the second sliding element 2106 and is configured to couple (temporarily or permanently) to the cap 2108. In some embodiments, the first end 2106A of the second sliding element 2106 and a second end 2108B of the cap 2108 may be threaded.

A second end 2106B of the second sliding element 2106 may be configured so that it can pass through a cavity 2110A in the spring 2110 and couple to the connection plate 2102 through the cavity 2102A. In one embodiment of the invention, the cap 2108 is configured as a counterpart to a cavity (not shown) in the mounting structure 2112 so that the cap 2108 can slide in and out of the cavity in the mounting structure 2112, when a first end 2108A of the cap 2108 is pressed to release or couple a gripper finger to the gripper unit 2000.

In one embodiment, the second sliding element 2106 has a round, axial cross section and can pass through the spring 2110. In one embodiment, the spring 2110 may be in uncompressed state so that the gripper finger release assembly 2010 is in a closed position (e.g., normal position) with a gripper finger coupled to the first sliding element 2104. In the closed position, the spring 2110 may be configured to urge the connection plate 2102 toward the cap 2108 such that the cap 2108 passes through a cavity in the mounting structure 2112 coupled to the body 2002. The spring 2110 may be a compression spring or any suitable biasing element for providing the appropriate force to keep the gripper finger release assembly 2010 in the closed position.

The cap 2108 may be cylindrical in shape with a diameter that exceeds the diameter of the second sliding element. In one embodiment, the cap 2108 may be configured so that when the cap 2108 is pushed or pressed, the cap 2108 slides into a cavity on the mounting structure 2112. Pushing the cap 2108 further enables the first sliding element 2104 to release the gripper finger due to the movement of the connection plate 2102 away from the mounting structure 2112.

A first gripper finger may be secured to the mounting structure 2112 by coupling to the first sliding element 2104. In embodiments of the invention, the first gripper finger may be released by pushing or pressing the cap 2108. The pushing or pressing the cap 2108 pushes the connection plate 2102 away from the mounting structure, thus uncoupling the gripper finger from the first sliding element 2104. After the first gripper finger has been released, a second gripper finger may be coupled to the first sliding element 2104 by keeping the cap 2108 pressed and aligning a cavity in the second gripper finger with the first end 2104A of the first sliding element 2104 and sliding the second gripper finger on to the first sliding element 2104. By releasing the cap 2108 pushes the gripper finger release assembly 2010 in a closed position by enabling the spring 2110 force the connection plate 2102 towards the mounting structure 2112 such that the cap 2108 slides out of the cavity of the mounting structure 2112.

In embodiments of the invention, the cap 2108 defines the space for the movement of the spring 2110 and also prevents the spring 2110 from getting lost.

Figure 5A:
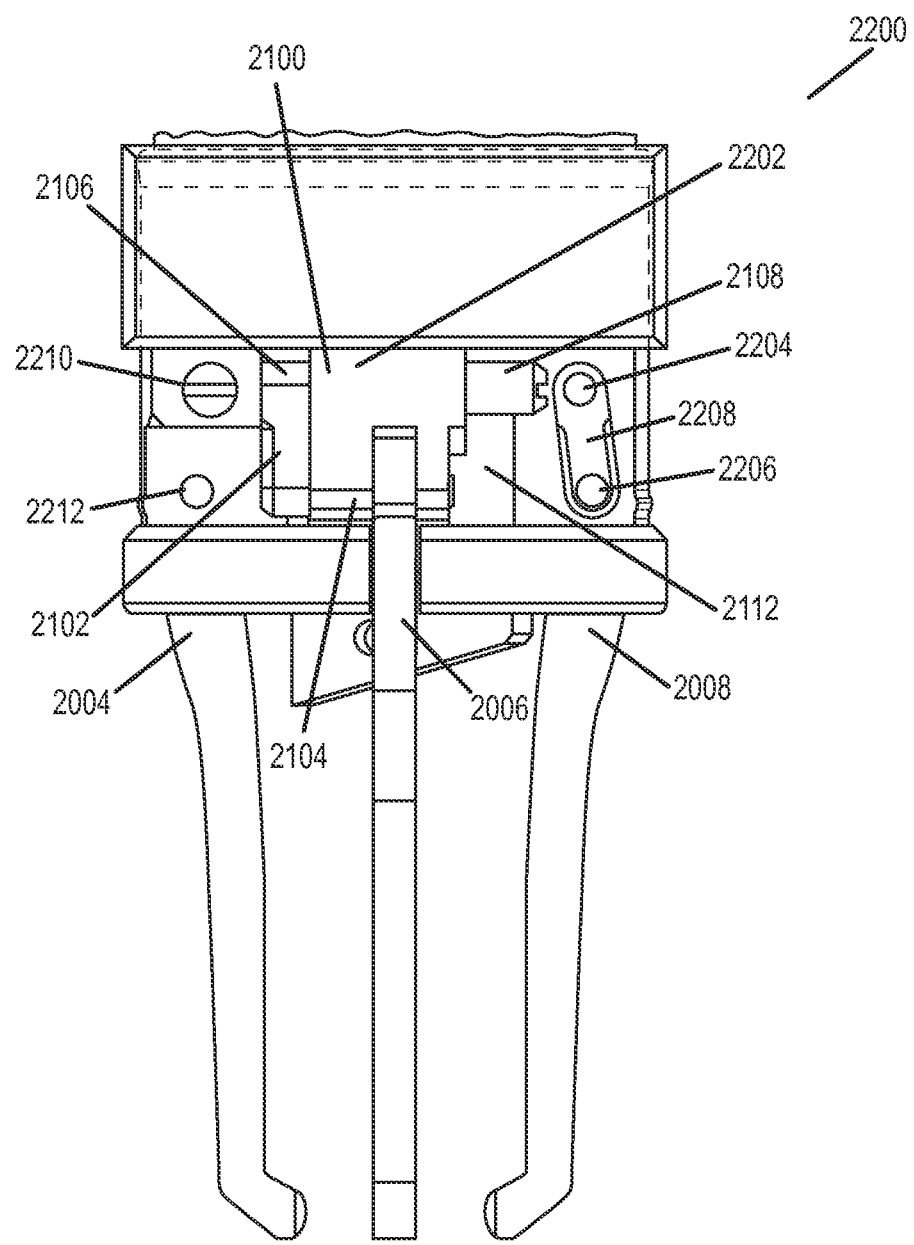
FIGS. 5A-5B illustrate the gripper finger release assembly in a closed position, in one embodiment of the invention.
Figure 5B:
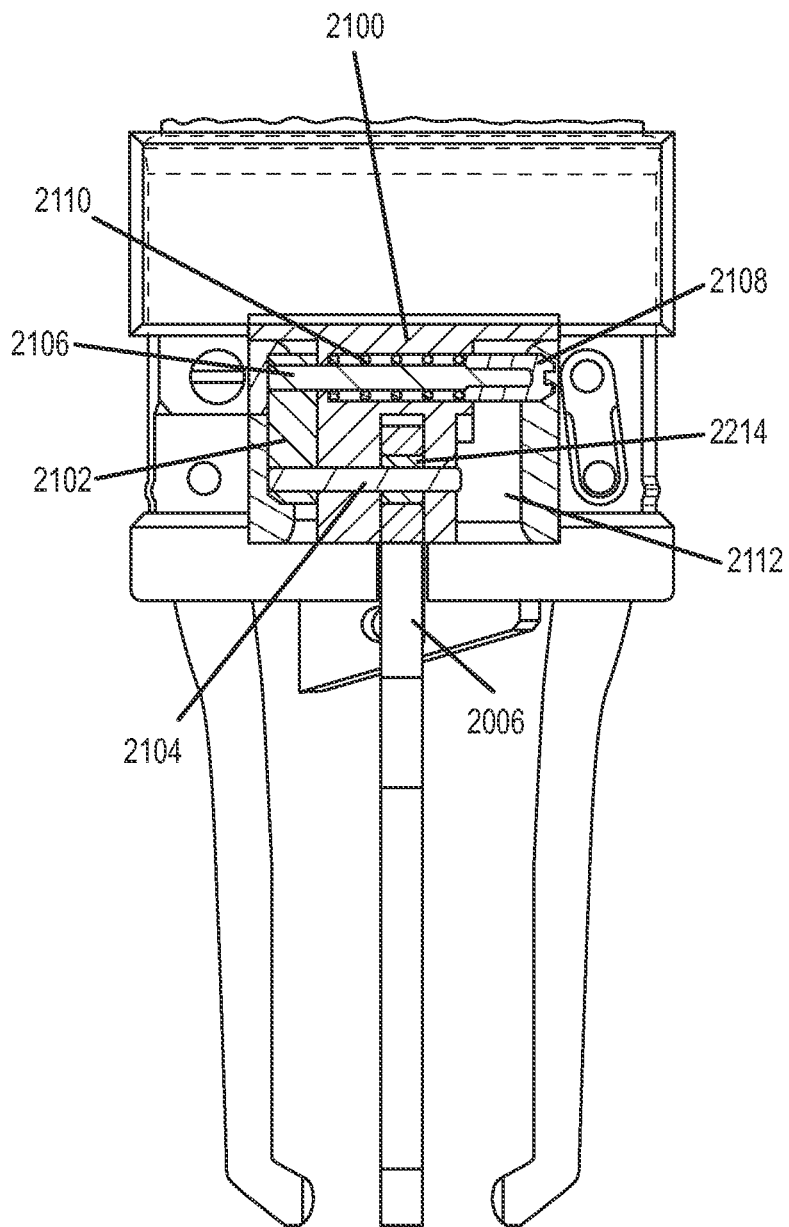

FIGS. 5A-5B illustrate the gripper finger release assembly in a closed position 2200, in one embodiment of the invention.

As illustrated in FIG. 5A, a cover 2202 may be coupled to the release element 2100 for covering at least some components of the release element 2100. The cover 2202 may be in a first position during the normal operation of the specimen gripper and in a second position during the exchange of the gripper fingers. In one embodiment, the cover 2202 may be in a closed position (first position) for the normal operation, as shown in FIG. 5A, and in an upward position (second position) for exchanging the fingers. The cover 2202 further protects the release element 2100 from contamination/pollution and maintains the closed position of the assembly during normal operation. It will be understood that various other configurations of the cover 2202 are possible.

As illustrated in FIG. 5A, cavities 2204, 2206 may be associated with a connection plate 2208 for a second release element configured for exchanging the gripper finger 2008. Similarly, cavities 2210, 2212 may be associated with a cap and a first end of a first sliding element respectively for a third release element configured for exchanging the gripper finger 2004. Note that each release element may have a cover (not shown) which may be in a first position during the normal operation of the specimen gripper and in a second position during the exchange of the respective gripper finger.

In the closed position of the gripper finger release assembly, the first sliding element 2104 may pass through a first cavity in the mounting structure 2112 and a cavity in the gripper finger 2006 to secure the gripper finger 2006 to the mounting structure 2112. The cap 2108 may be pushed out from the force of the spring 2110 (not shown in FIG. 5A)

through a second cavity in the mounting structure 2112. An internal, cross-sectional view of the gripper finger release assembly in the closed position is shown in FIG. 5B.

In one embodiment, the gripper finger 2006 may be coupled to the first sliding element 2104 through a bushing 2214 or any other suitable component, as illustrated in FIG. 5B. The bushing 2214 may be made of rubber or any such suitable material and may be configured to allow coupling of the gripper finger 2006 to the first sliding element 2104.

Figure 6:
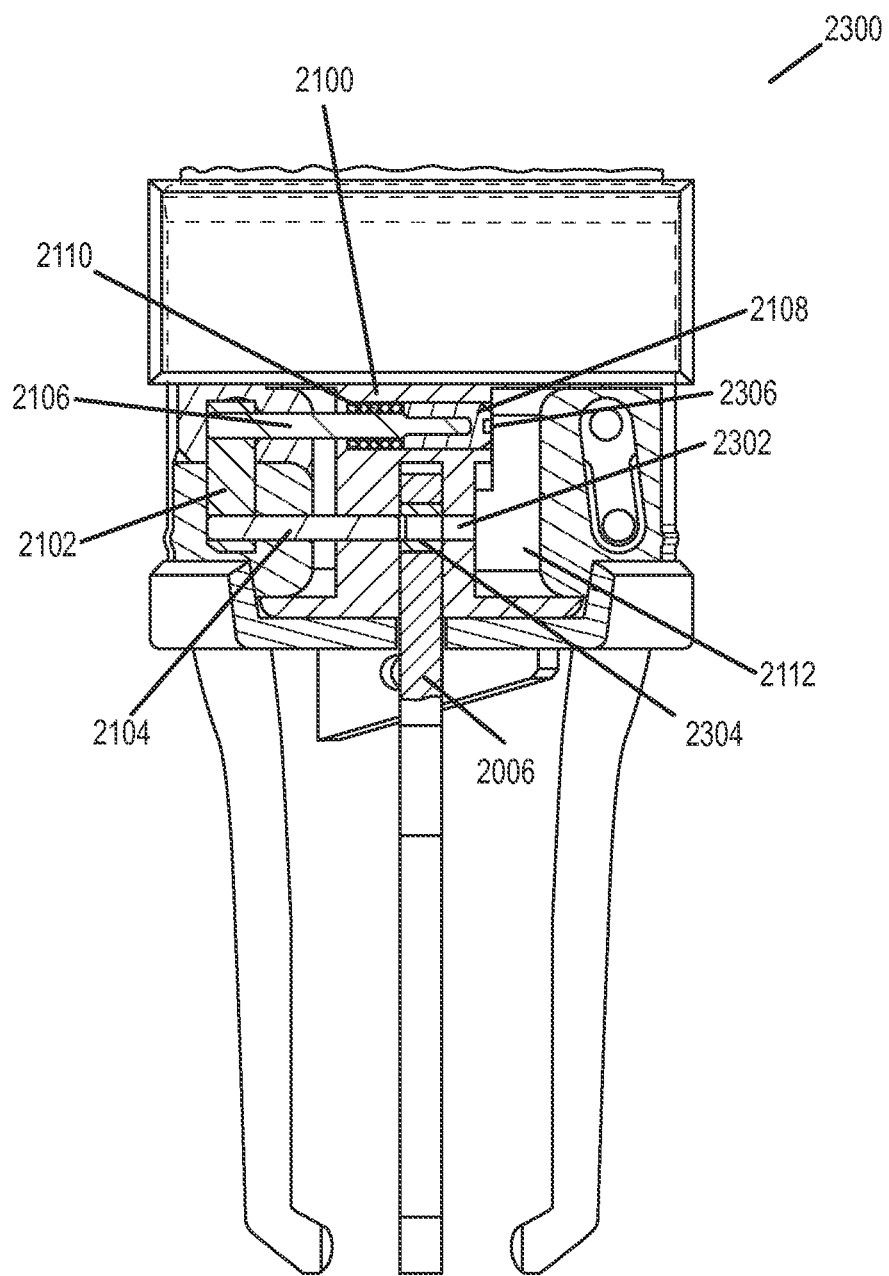
FIG. 6 illustrates the gripper finger release assembly in an open position, in one embodiment of the invention.

FIG. 6 illustrates an inside view of the gripper finger release assembly in an open position 2300, in one embodiment of the invention.

As illustrated in FIG. 6, the first sliding element 2104 may be configured to pass through a cavity 2304 in the gripper finger 2006 and a cavity 2302 in the mounting structure 2112 to secure the gripper finger 2006 to the mounting structure 2112. In order to open the gripper finger release assembly for releasing or exchanging a gripper finger, the cap 2108 may be pressed until the head of the cap 2108 is leveled with a surface of the mounting structure 2112 through a cavity 2306 in the mounting structure 2112. Note that the pressing of the cap 2108 pushes the connection plate 2102 away from the mounting structure 2112 and keeps the spring 2110 in a compressed state. This enables the first sliding element 2104 to slide out of the cavity 2304 in the gripper finger 2006, thus releasing or uncoupling the gripper finger 2006.

In some embodiments, the cavity 2302 may be substituted for a bushing, which may be pressed in the mounting structure 2112.

Referring back to FIG. 5B, as compared to the open position of the gripper finger release assembly, the first sliding element 2104 is pushed out from the cavity 2304 of the gripper finger 2006. This allows the uncoupling of the gripper finger 2006 from the specimen gripper. In this position a new gripper finger may be coupled to the first sliding element 2104 by keeping the cap 2108 pressed and by sliding the new gripper finger on the first sliding element 2104 through a cavity in the new gripper finger. Once the new gripper finger is coupled to the first sliding element 2104, the cap 2108 may be released which enables the spring 2110 to uncompress and push the cap 2108 out of the cavity 2306 in the mounting structure 2112 and bring the gripper finger release assembly to a closed or locked position.

Embodiments of the invention provide a method to replace a first gripper finger with a second gripper finger using a release element, for example, the release element 2100.

In a first step of the method, the first gripper finger may be removably coupled to a mounting structure by the release element. The first gripper finger may comprise a first cavity and the mounting structure may comprise a second cavity. The release element may comprise a plate, a first sliding element coupled to the plate and a second sliding element coupled to the plate. The first sliding element may be configured to pass through the first and second cavities to secure the first gripper finger to the mounting structure. Referring back to FIG. 6, the first gripper finger may be removably coupled to the mounting structure 2112 by the release element 2100. For example, the first sliding element 2104 may pass through a first cavity in the first gripper finger (similar to the cavity 2304) and the cavity 2302 in the mounting structure 2112.

In a second step of the method, the first gripper finger may be released by pressing the second sliding element. For example, by pressing the cap 2108 presses the second sliding element 2106, thus enabling the first sliding element 2104 to slide out of the cavities 2304 and 2302 and release the first gripper finger.

In a third step of the method, a third cavity on the second gripper finger may be aligned with the first sliding element after the first gripper finger has been released. For example, the third cavity (similar to the cavity 2304) on the second gripper finger may be aligned with the first sliding element 2104 so that the first sliding element 2104 can easily pass through it.

In a fourth step of the method, the second gripper finger may be removably coupled to the first sliding element by releasing the second sliding element. For example, by releasing the second sliding element 2106 (or the cap 2108) enables the spring 2110 to uncompress and push the second sliding element 2106 (or the cap 2108) out of the cavity 2306 in the mounting structure 2112, thus coupling the second gripper finger to the first sliding element 2104.

Embodiments of the invention provide advantages since no tool is required for exchanging the gripper fingers. The gripper finger release assembly can be unlocked with only one movement by using a small force to overcome the force of the spring. Further, the spring gets no load since bearing of forces is separated from the closing feature. Embodiments of the invention prevent twisting of the gripper fingers relative to the specimen gripper due to the inherent configuration of the release element 2100.

Figure 7:
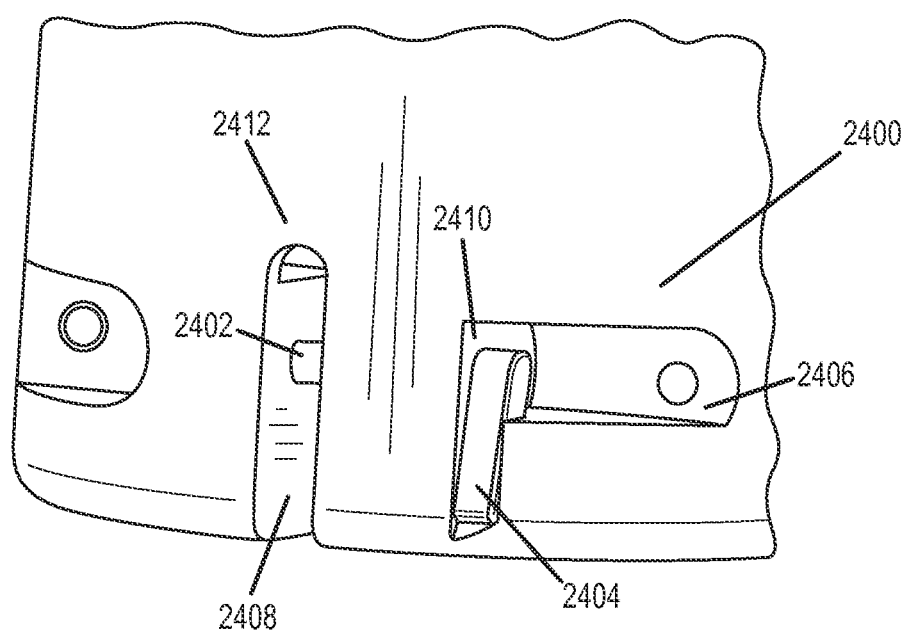
FIG. 7 illustrates a release element in a second embodiment of the invention.

FIG. 7 illustrates a release element 2400 in a second embodiment of the invention.

In one embodiment, the release element 2400 may be part of the gripper finger release assembly 2010. The release element 2400 may comprise a post (or a sliding element) 2402 coupled to a plate 2410. The plate 2410 may be a part of or coupled to a mounting structure 2412. In one embodiment, the mounting structure 2412 is part of the body 1116 of the gripper unit 1114.

The post 2402 may be similar to the first sliding element 2104 (as shown in FIGS. 4A-4B) and may have a cylindrical shape with a circular cross-section. The post 2402 may be configured to removably couple to a gripper finger (e.g., one of the gripper fingers 1118) within a gripper finger slot 2408 and further be configured to pass through a cavity in the gripper finger and a cavity in the mounting structure 2412 to secure the gripper finger to the mounting structure 2412. The cavity in the gripper finger may be similar to the cavity 2304 of the gripper finger 2006, as shown in FIG. 6, with a diameter slightly larger than the diameter of the post 2402 so that the post 2402 can pass through the cavity of the gripper finger.

In one embodiment, a lever 2404 may be coupled to the plate 2410 and the post 2402 and configured to control the movement of the post 2402 within the gripper finger slot 2408. In one embodiment, the lever 2404 may be configured to enable the post 2402 to release a first gripper finger coupled to the post 2402 by rotation of the lever 2404. For example, the lever 2404 can be rotated (e.g., by approximately 90 degrees) and pulled away from the gripper finger slot 2408 (e.g., to the right or counterclockwise, in accordance with the illustrative example shown in FIG. 7) to release the first gripper finger. A groove 2406 in the mounting structure 2412 may be configured to accommodate the post 2402 when the post 2402 has been removed from the gripper finger slot 2408.

In one embodiment, rotating the lever 2404 in a second direction (e.g., to the left or clockwise, as shown in the illustrative example of FIG. 7) may slide the post 2402 into the gripper finger slot 2408 so that a second gripper finger may be coupled to the post 2402.

Figure 8A:
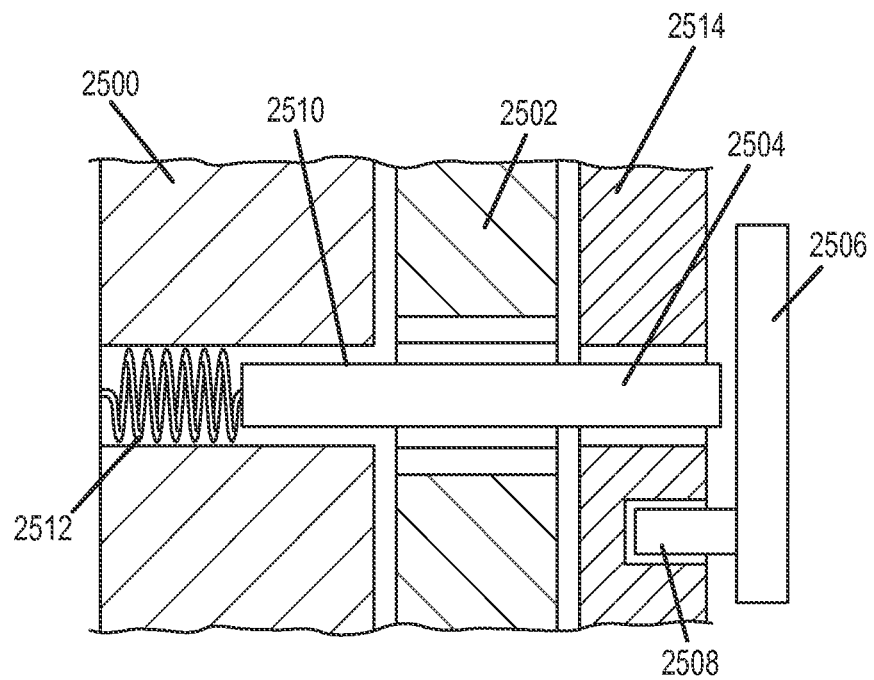
FIGS. 8A-8C illustrate a release element in a third embodiment of the invention.
Figure 8B:
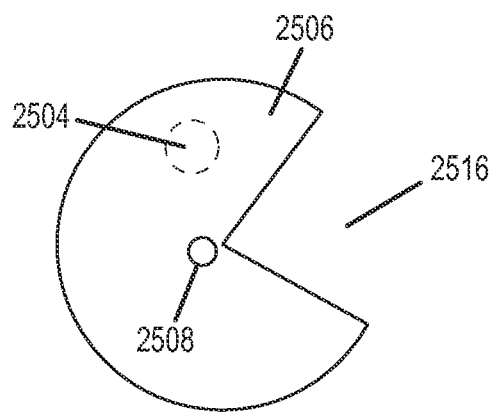
Figure 8C:
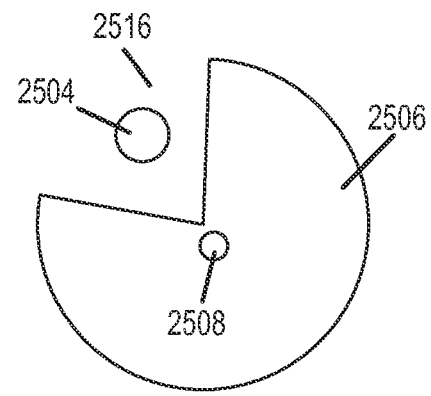

FIGS. 8A-8C illustrate a release element 2500 in a third embodiment of the invention.

In one embodiment, the release element 2500 may be part of the gripper finger release assembly 2010. The release element 2500 may comprise a post (or a sliding element) 2504 coupled to a plate 2506. A gripper finger 2502 may be removably coupled to the post 2504. The plate 2506 may be a part of or coupled to a mounting structure 2514. In one embodiment, the mounting structure 2514 is part of the body 1116 of the gripper unit 1114. A spring 2512 may be coupled to the mounting structure 2514 configured to be in contact with the post 2504.

The post 2402 may be similar to the first sliding element 2104 (as shown in FIGS. 4A-4B) and may have a cylindrical shape with a circular cross-section. The post 2402 may be configured to pass through a cavity in the gripper finger 2502 and a cavity in the mounting structure 2514 to secure the gripper finger 2502 to the mounting structure 2514. The cavity in the gripper finger 2502 may be similar to the cavity 2304 of the gripper finger 2006, as shown in FIG. 6, with a diameter slightly larger than the diameter of the post 2504 so that the post 2504 can pass through the cavity of the gripper finger 2502.

In one embodiment, the plate 2506 is configured as a rotating plate that can be pivoted about an axis defined by a pin 2508 coupled to the plate 2506. The pin 2508 may also be coupled to the mounting structure 2514 and configured to enable the rotation of the plate 2506 in a clockwise or a counter clock wise direction relative to the pin 2508, as discussed with reference to FIGS. 8B-8C.

As illustrated in FIGS. 8B-8C, in one embodiment, the plate 2506 may be circular in shape with an opening 2516 relatively larger than the diameter of the post 2504 in order to allow the post 2504 pass through the opening 2516 when the plate 2506 is rotated. It will be understood that any configuration of the plate 2506 and the opening 2516 is possible in order to allow the post 2504 to pass though the opening 2516.

FIG. 8B illustrates a closed position of the plate 2506, in which the post 2504 is confined in a cavity 2510 behind the rotating plate 2506. In this position the gripper finger 2502 may be coupled to the post 2504 and the spring 2512 may be in a compressed state.

FIG. 8C illustrates an open position of the plate 2506, in which the post 2504 is released through the opening 2516 of the rotating plate 2506. The spring 2512 urges the post 2504 towards the opening 2516, thus allowing the post 2504 to be extract from the cavity 2510. When the post 2504 is extracted, the gripper finger 2502 can be removed and replaced with another gripper finger.

As discussed above, a first gripper finger comprising a first cavity may be removably coupled to a mounting structure comprising a second cavity by a release element. The release element may be the release element 2100, release element 2400 or the release element 2500. The release element may comprise a plate and a first sliding element coupled to the plate, and wherein the first sliding element is configured to pass through the first and second cavities to secure the first gripper finger to the mounting structure. The first gripper finger may be released by enabling the first sliding element to slide out of the first and second cavities. After the first gripper finger has been released, a third cavity on a second gripper finger is aligned with the first sliding element to removably couple the second gripper finger to the first sliding element.

Embodiments of the invention provide quick one-handed exchange of gripper fingers without the need of tools or without demounting or mounting of the gripper finger release assembly from the specimen gripper. Thus, embodiments allow quick exchange of gripper fingers, for example, to change the function of the specimen gripper, e.g., as a tube gripper, recapper or a decapper.

Computer Architecture

The various participants and elements described herein with reference to FIG. 2 may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 9:
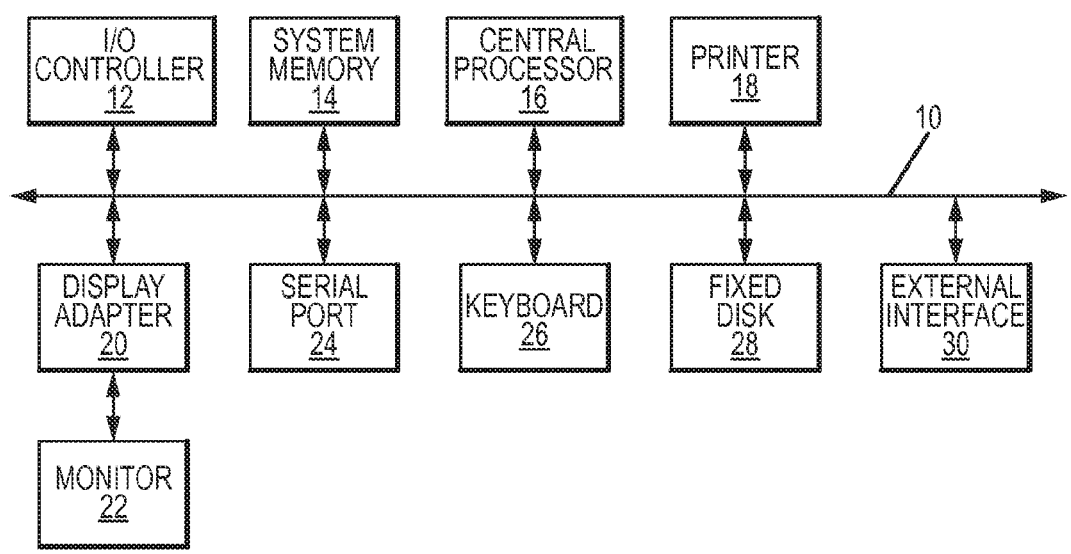
FIG. 9 depicts a block diagram of an exemplary computer apparatus.

Examples of such subsystems or components are shown in FIG. 9. The subsystems shown in FIG. 9 are interconnected via a system bus 10. Additional subsystems such as a printer 18, keyboard 26, fixed disk 28 (or other memory comprising computer readable media), monitor 22, which is coupled to display adapter 20, and others are shown. Peripherals and input/output (I/O) devices, which couple to I/O controller 12 (which can be a processor or other suitable controller), can be connected to the computer system by any number of means known in the art, such as serial port 24. For example, serial port 24 or external interface 30 can be used to connect the computer apparatus to a wide area network such as the Internet, a mouse input device, or a scanner. The interconnection via system bus allows the central processor 16 to communicate with each subsystem and to control the execution of instructions from system memory 14 or the fixed disk 28, as well as the exchange of information between subsystems. The system memory 14 and/or the fixed disk 28 may embody a computer readable medium.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A gripper unit for gripping a tube, the gripper unit comprising:
   a plurality of release elements;
   a plurality of elongated gripper fingers respectively associated with the plurality of release elements, the plurality of elongated gripper fingers adapted to move inward to grip the tube and outward to release the tube, the plurality of elongated gripper fingers comprising a plurality of first cavities, respectively;
   a mounting structure comprising a plurality of second cavities,
   wherein the plurality of elongated gripper fingers are removably coupled to the mounting structure by the plurality of release elements, respectively,
   wherein each release element comprises a plate, and a first sliding element and a second sliding element coupled to the plate, wherein the first sliding element is configured to pass through a first cavity in an elongated gripper finger in the plurality of elongated gripper fingers and a second cavity in the mounting structure to secure the elongated gripper finger to the mounting structure and to allow the elongated gripper finger to pivot inward about the first sliding element to grip the tube and outward about the first sliding element to release the tube, and
   wherein the second sliding element is configured to enable the first sliding element to release the elongated gripper finger when the second sliding element is pressed.

2. The gripper unit of claim 1, further comprising a cap, wherein the second sliding element is coupled to the cap, and wherein the second sliding element is longer than the first sliding element.

3. The gripper unit of claim 2, wherein the cap is configured to pass through a third cavity on the mounting structure.

4. The gripper unit of claim 1, further comprising:
   a spring coupled to the second sliding element, the spring configured to push the plate towards the mounting structure.

5. A system comprising the gripper unit of claim 1.

6. The gripper unit of claim 1 wherein the longitudinal direction of each elongated gripper finger is perpendicular to the orientation of the first sliding element of a corresponding release element by means of which the respective elongated gripper finger is attached to the mounting structure.

7. The gripper unit of claim 1 wherein the front ends of the plurality of elongated gripper fingers face downward and the first sliding element is horizontal.

8. A gripper unit comprising:
   a release element;
   a first elongated gripper finger comprising a first cavity;
   a mounting structure comprising a second cavity,
   wherein the first elongated gripper finger is removably coupled to the mounting structure by the release element, and wherein the release element comprises a first sliding element, wherein the first sliding element is configured to pass through the first and second cavities to secure the first elongated gripper finger to the mounting structure; and
   wherein the gripper unit further comprises a spring operatively coupled to the first sliding element; and
   wherein the release element further comprises a plate, and a pin coupled to the plate and to the mounting structure,
   wherein the plate is configured to pivot about an axis defined by the pin to release the first elongated gripper finger.

9. The gripper unit of claim 8, wherein the spring is configured to urge the first sliding element to slide out from an opening in the plate to release the first elongated gripper finger, when the plate is rotated.

10. A method comprising:
    removably coupling a plurality of elongated gripper fingers, each comprising a first cavity, to a mounting structure of a gripper unit, adapted for gripping a tube, the mounting structure comprising a plurality of second cavities, by a plurality of release elements, wherein each release element comprises a plate, a first sliding element coupled to the plate and a second sliding element coupled to the plate, and wherein each first sliding element is configured to pass through both the first cavity of an elongated gripper finger out of the plurality of elongated gripper fingers and a second cavity of the mounting structure to secure the elongated gripper finger to the mounting structure, wherein each elongated gripper finger pivots about the first sliding element when the plurality of elongated gripper fingers moves inward to grip the tube or moves outward to release the tube; and
    gripping or releasing the tube.

11. The method of claim 10, wherein the plurality of release elements comprises a first release element and wherein the plurality of elongated gripper fingers comprises a first elongated gripper finger, and wherein the method further comprises:
    pressing the second sliding element of the first release element to remove the first sliding element of the first release element from the first cavity of the first elongated gripper finger to release said first elongated gripper finger from the mounting structure,
    removing the first elongated gripper finger from the mounting structure,
    aligning the first cavity of a second elongated gripper finger with the first sliding element of the first release element; and
    removably coupling the second elongated gripper finger to the first sliding element of the first release element by releasing the second sliding element.

12. The method of claim 10 wherein the longitudinal direction of each elongated gripper finger is perpendicular to the orientation of the first sliding element of a corresponding release element by means of which the respective elongated gripper finger is attached to the mounting structure.

* * * * *